(12) United States Patent
Robaina et al.

(10) Patent No.: US 7,951,193 B2
(45) Date of Patent: May 31, 2011

(54) DRUG-ELUTING STENT

(75) Inventors: Samuel Robaina, Santa Rosa, CA (US); Cory Hitzman, St. Paul, MN (US); Kim Robertson, Forest Lake, MN (US); Liza Davis, St. Michael, MN (US); Jason T. Lenz, Maplewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 21 days.

(21) Appl. No.: 12/178,180

(22) Filed: Jul. 23, 2008

(65) Prior Publication Data

US 2010/0023115 A1 Jan. 28, 2010

(51) Int. Cl.
*A61F 2/06* (2006.01)
(52) U.S. Cl. ......... 623/1.42; 623/1.43; 623/1.15
(58) Field of Classification Search ......... 623/1.15, 623/1.39, 1.42, 1.44, 1.46
See application file for complete search history.

(56) References Cited

U.S. PATENT DOCUMENTS

| | | | |
|---|---|---|---|
| 3,948,254 A | 4/1976 | Zaffaroni | |
| 4,784,659 A | 11/1988 | Flecksenstein et al. | |
| 5,338,296 A | 8/1994 | Dalessandro et al. | |
| 5,449,382 A | 9/1995 | Dayton | |
| 5,464,650 A | 11/1995 | Berg et al. | |
| 5,605,696 A | 2/1997 | Eury et al. | |
| 5,609,629 A | 3/1997 | Fearnot et al. | |
| 5,797,898 A | 8/1998 | Santini, Jr. et al. | |
| 5,843,172 A | 12/1998 | Yan | |
| 5,891,108 A | 4/1999 | Leone et al. | |
| 5,922,021 A | 7/1999 | Jang | |
| 5,972,027 A | 10/1999 | Johnson | |
| 5,980,564 A | 11/1999 | Stinson | |
| 6,063,101 A | 5/2000 | Jacobsen et al. | |
| 6,071,305 A | 6/2000 | Brown et al. | |
| 6,190,404 B1 | 2/2001 | Palmaz et al. | |
| 6,206,915 B1 | 3/2001 | Fagan et al. | |
| 6,214,042 B1 | 4/2001 | Jacobsen et al. | |
| 6,240,616 B1 | 6/2001 | Yan | |
| 6,241,762 B1 | 6/2001 | Shanley | |
| 6,254,632 B1 | 7/2001 | Wu et al. | |
| 6,273,908 B1 | 8/2001 | Ndondo-Lay | |
| 6,273,913 B1 | 8/2001 | Wright et al. | |
| 6,287,628 B1 | 9/2001 | Hossainy et al. | |
| 6,299,604 B1 | 10/2001 | Ragheb et al. | |
| 6,325,825 B1 | 12/2001 | Kula et al. | |
| 6,379,382 B1 | 4/2002 | Yang | |
| 6,395,326 B1 | 5/2002 | Castro et al. | |
| 6,471,721 B1 | 10/2002 | Dang | |
| 6,471,980 B2 | 10/2002 | Sirhan et al. | |

(Continued)

FOREIGN PATENT DOCUMENTS

DE 3516411 11/1986

(Continued)

*Primary Examiner* — Corrine M McDermott
*Assistant Examiner* — Seema Swaminathan
(74) *Attorney, Agent, or Firm* — Vidas, Arrett & Steinkraus (57) ABSTRACT

A stent for delivering therapeutic agents to a body lumen includes a plurality of circumferential serpentine bands with each band comprising a plurality of struts. At least one strut has at least one first well region and at least one second well region. The at least one first well region has a first thickness, the at least one second well region has a second thickness, the first thickness being greater than the second thickness. Each well region defines a well having a depth. At least some of the wells contain a therapeutic agent.

7 Claims, 6 Drawing Sheets

U.S. PATENT DOCUMENTS

| | | |
|---|---|---|
| 6,506,437 B1 | 1/2003 | Harish et al. |
| 6,517,858 B1 | 2/2003 | Le Moel et al. |
| 6,521,284 B1 | 2/2003 | Parsons et al. |
| 6,527,938 B2 | 3/2003 | Bales et al. |
| 6,544,582 B1 | 4/2003 | Yoe |
| 6,558,422 B1 | 5/2003 | Baker et al. |
| 6,558,733 B1 | 5/2003 | Hossainy et al. |
| 6,585,765 B1 | 7/2003 | Hossainy et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,581 B1 | 11/2003 | Ding |
| 6,660,034 B1 | 12/2003 | Mandrusov et al. |
| 6,663,664 B1 | 12/2003 | Pacetti |
| 6,709,379 B1 | 3/2004 | Brandau et al. |
| 6,709,451 B1 | 3/2004 | Noble et al. |
| 6,716,444 B1 | 4/2004 | Castro et al. |
| 6,725,901 B1 | 4/2004 | Kramer et al. |
| 6,730,120 B2 | 5/2004 | Berg et al. |
| 6,752,826 B2 | 6/2004 | Holloway et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,776,022 B2 | 8/2004 | Kula et al. |
| 6,780,424 B2 | 8/2004 | Claude |
| 6,805,898 B1 | 10/2004 | Wu et al. |
| 6,815,609 B1 | 11/2004 | Wang et al. |
| 6,846,323 B2 | 1/2005 | Yip et al. |
| 6,875,227 B2 | 4/2005 | Yoon |
| 6,884,429 B2 | 4/2005 | Koziak et al. |
| 6,896,697 B1 | 5/2005 | Yip et al. |
| 6,913,617 B1 | 7/2005 | Reiss |
| 6,918,927 B2 | 7/2005 | Bates et al. |
| 6,955,685 B2 | 10/2005 | Escamilla et al. |
| 6,962,822 B2 | 11/2005 | Hart et al. |
| 6,973,718 B2 | 12/2005 | Sheppard, Jr. et al. |
| 6,979,347 B1 | 12/2005 | Wu et al. |
| D516,723 S | 3/2006 | Shanley |
| 7,044,965 B1 | 5/2006 | Spielberg |
| 7,070,617 B2 | 7/2006 | Kula et al. |
| 7,105,018 B1 | 9/2006 | Yip et al. |
| 7,114,312 B2 | 10/2006 | Coppeta et al. |
| 7,135,038 B1 | 11/2006 | Limon |
| 7,135,039 B2 * | 11/2006 | De Scheerder et al. ...... 623/1.42 |
| 7,160,321 B2 | 1/2007 | Shanley |
| 7,163,555 B2 | 1/2007 | Dinh |
| 7,163,715 B1 | 1/2007 | Kramer |
| 7,169,178 B1 | 1/2007 | Santos et al. |
| 7,223,282 B1 | 5/2007 | Hossainy |
| 7,229,413 B2 | 6/2007 | Violante et al. |
| 7,229,471 B2 | 6/2007 | Gale et al. |
| 7,238,199 B2 | 7/2007 | Feldman et al. |
| 7,244,442 B2 | 7/2007 | Williams et al. |
| 7,309,353 B2 | 12/2007 | Krivoruchko |
| 7,316,710 B1 | 1/2008 | Cheng et al. |
| 7,335,314 B2 | 2/2008 | Wu et al. |
| 7,393,359 B2 | 7/2008 | Verin et al. |
| 7,410,498 B2 | 8/2008 | Penhasi |
| 7,413,846 B2 | 8/2008 | Maloney et al. |
| 7,416,559 B2 | 8/2008 | Shalaby |
| 7,425,217 B2 | 9/2008 | Maier et al. |
| 7,455,753 B2 | 11/2008 | Roth |
| 2002/0038145 A1 * | 3/2002 | Jang ............................. 623/1.15 |
| 2002/0038146 A1 | 3/2002 | Harry |
| 2002/0103527 A1 | 8/2002 | Kocur et al. |
| 2002/0103528 A1 | 8/2002 | Schaldach et al. |
| 2002/0120326 A1 | 8/2002 | Michal |
| 2002/0123801 A1 | 9/2002 | Pacetti et al. |
| 2002/0138136 A1 | 9/2002 | Chandresekaran et al. |
| 2002/0155212 A1 | 10/2002 | Hossainy |
| 2002/0183721 A1 | 12/2002 | Santini et al. |
| 2002/0193336 A1 | 12/2002 | Elkins et al. |
| 2003/0032892 A1 | 2/2003 | Erlach et al. |
| 2003/0060871 A1 | 3/2003 | Hill et al. |
| 2003/0064095 A1 | 4/2003 | Martin et al. |
| 2003/0069631 A1 | 4/2003 | Stoll |
| 2003/0088312 A1 | 5/2003 | Kopia et al. |
| 2003/0104590 A1 | 6/2003 | Santini, Jr. et al. |
| 2003/0105511 A1 | 6/2003 | Welsh et al. |
| 2003/0105512 A1 | 6/2003 | Kanesaka |
| 2003/0153901 A1 | 8/2003 | Herweck et al. |
| 2003/0216803 A1 | 11/2003 | Ledergerber |
| 2004/0000540 A1 | 1/2004 | Soboyejo et al. |
| 2004/0034337 A1 | 2/2004 | Boulais et al. |
| 2004/0043042 A1 | 3/2004 | Johnson et al. |
| 2004/0088038 A1 | 5/2004 | Dehnad et al. |
| 2004/0093076 A1 | 5/2004 | White et al. |
| 2004/0098089 A1 | 5/2004 | Weber |
| 2004/0117008 A1 | 6/2004 | Wnendt et al. |
| 2004/0133270 A1 | 7/2004 | Grandt |
| 2004/0142014 A1 | 7/2004 | Litvack et al. |
| 2004/0143321 A1 | 7/2004 | Litvack et al. |
| 2004/0148010 A1 | 7/2004 | Rush |
| 2004/0167572 A1 | 8/2004 | Roth et al. |
| 2004/0202692 A1 | 10/2004 | Shanley et al. |
| 2004/0204750 A1 | 10/2004 | Dinh |
| 2004/0211362 A1 | 10/2004 | Castro et al. |
| 2004/0236416 A1 | 11/2004 | Falotico |
| 2004/0237282 A1 | 12/2004 | Hines |
| 2004/0247671 A1 | 12/2004 | Prescott et al. |
| 2004/0249449 A1 | 12/2004 | Shanley et al. |
| 2005/0015142 A1 | 1/2005 | Austin et al. |
| 2005/0021127 A1 | 1/2005 | Kawula |
| 2005/0027350 A1 | 2/2005 | Momma et al. |
| 2005/0033417 A1 | 2/2005 | Borges et al. |
| 2005/0055080 A1 | 3/2005 | Istephanous et al. |
| 2005/0060020 A1 | 3/2005 | Jensen |
| 2005/0060021 A1 | 3/2005 | O'Brien et al. |
| 2005/0074545 A1 | 4/2005 | Thomas |
| 2005/0079199 A1 | 4/2005 | Heruth et al. |
| 2005/0095267 A1 | 5/2005 | Campbell et al. |
| 2005/0106212 A1 | 5/2005 | Gertner et al. |
| 2005/0119723 A1 | 6/2005 | Peacock |
| 2005/0136090 A1 | 6/2005 | Falotico et al. |
| 2005/0137677 A1 | 6/2005 | Rush |
| 2005/0137679 A1 | 6/2005 | Changelian et al. |
| 2005/0137684 A1 | 6/2005 | Changelian et al. |
| 2005/0159805 A1 | 7/2005 | Weber et al. |
| 2005/0171595 A1 | 8/2005 | Feldman et al. |
| 2005/0192657 A1 | 9/2005 | Colen et al. |
| 2005/0196424 A1 | 9/2005 | Chappa |
| 2005/0208100 A1 | 9/2005 | Weber et al. |
| 2005/0209681 A1 | 9/2005 | Curcio et al. |
| 2005/0228477 A1 | 10/2005 | Grainger et al. |
| 2005/0228491 A1 | 10/2005 | Snyder et al. |
| 2005/0232968 A1 | 10/2005 | Palmaz et al. |
| 2005/0234538 A1 | 10/2005 | Litvack et al. |
| 2005/0251245 A1 | 11/2005 | Sieradzki et al. |
| 2005/0256564 A1 | 11/2005 | Yang et al. |
| 2005/0261757 A1 | 11/2005 | Shanley |
| 2005/0266039 A1 | 12/2005 | Weber |
| 2005/0266040 A1 | 12/2005 | Gerberding |
| 2005/0271696 A1 | 12/2005 | Dinn et al. |
| 2005/0278929 A1 | 12/2005 | Lee |
| 2005/0283225 A1 | 12/2005 | Klisch |
| 2005/0287287 A1 | 12/2005 | Parker et al. |
| 2006/0025848 A1 | 2/2006 | Weber et al. |
| 2006/0034884 A1 | 2/2006 | Stenzel |
| 2006/0052744 A1 | 3/2006 | Weber |
| 2006/0053618 A1 | 3/2006 | Verin et al. |
| 2006/0069427 A1 | 3/2006 | Savaget et al. |
| 2006/0085065 A1 | 4/2006 | Krause et al. |
| 2006/0100608 A1 | 5/2006 | Uhland et al. |
| 2006/0129215 A1 | 6/2006 | Helmus et al. |
| 2006/0129225 A1 | 6/2006 | Kopia |
| 2006/0136051 A1 | 6/2006 | Furst et al. |
| 2006/0161264 A1 | 7/2006 | Ferreyrol |
| 2006/0171989 A1 | 8/2006 | Prescott et al. |
| 2006/0198750 A1 | 9/2006 | Furst et al. |
| 2006/0200229 A1 | 9/2006 | Bugermeister et al. |
| 2006/0217801 A1 | 9/2006 | Rosenthal |
| 2006/0224234 A1 | 10/2006 | Jayaraman |
| 2006/0224237 A1 | 10/2006 | Furst et al. |
| 2006/0229713 A1 | 10/2006 | Shanley |
| 2006/0235504 A1 | 10/2006 | Gonzales |
| 2006/0259005 A1 | 11/2006 | Konstantino et al. |
| 2006/0269475 A1 | 11/2006 | Ryu et al. |

| | | | | | | |
|---|---|---|---|---|---|---|
| 2006/0275341 | A1 | 12/2006 | Liv et al. | EP | 1254673 | 11/2002 |
| 2007/0027530 | A1 | 2/2007 | Saint et al. | EP | 1277449 | 1/2003 |
| 2007/0032430 | A1 | 2/2007 | Fogelman et al. | EP | 1308179 | 5/2003 |
| 2007/0038176 | A1 | 2/2007 | Weber et al. | EP | 1310242 | 5/2003 |
| 2007/0043423 | A1 | 2/2007 | Grewe | EP | 1348402 | 10/2003 |
| 2007/0055352 | A1 | 3/2007 | Naimark et al. | EP | 1362603 | 11/2003 |
| 2007/0065418 | A1 | 3/2007 | Vallana | EP | 1402849 | 3/2004 |
| 2007/0065477 | A1 | 3/2007 | Parker et al. | EP | 1449546 | 8/2004 |
| 2007/0073385 | A1 | 3/2007 | Schaeffer et al. | EP | 1319416 | 11/2004 |
| 2007/0100438 | A1 | 5/2007 | Civelli | EP | 1011529 | 1/2005 |
| 2007/0110786 | A1 | 5/2007 | Tenney | EP | 1570808 | 9/2005 |
| 2007/0110888 | A1 | 5/2007 | Radhakrishnan et al. | EP | 1604697 | 12/2005 |
| 2007/0112414 | A1 | 5/2007 | Parker et al. | EP | 1685861 A2 | 8/2006 |
| 2007/0112416 | A1 | 5/2007 | Shanley et al. | EP | 1359865 | 11/2006 |
| 2007/0112417 | A1 | 5/2007 | Shanley et al. | EP | 1779816 | 5/2007 |
| 2007/0112421 | A1 | 5/2007 | O'Brien | EP | 1886703 | 2/2008 |
| 2007/0151638 | A1 | 7/2007 | Burgermeister et al. | EP | 1891988 | 2/2008 |
| 2007/0173923 | A1 | 7/2007 | Savage et al. | EP | 1891995 | 2/2008 |
| 2007/0191816 | A1 | 8/2007 | Behan et al. | EP | 1935508 | 6/2008 |
| 2007/0202147 | A1 | 8/2007 | Kleiner et al. | EP | 1952789 | 8/2008 |
| 2007/0219628 | A1 | 9/2007 | Shanley et al. | GB | 012198.7 | 9/2001 |
| 2007/0224116 | A1 | 9/2007 | Chandrasekaran et al. | GB | 2397233 | 7/2004 |
| 2007/0224235 | A1 | 9/2007 | Tenney et al. | JP | 2005160600 | 6/2005 |
| 2007/0255393 | A1 | 11/2007 | Flanagan | JP | 2006175017 | 7/2006 |
| 2007/0259116 | A1 | 11/2007 | Nolan et al. | WO | 9306792 | 4/1993 |
| 2008/0051881 | A1 | 2/2008 | Feng et al. | WO | 9838946 | 9/1998 |
| 2008/0057101 | A1 | 3/2008 | Roorda | WO | 0037138 | 6/2000 |
| 2008/0071344 | A1 | 3/2008 | Silberg et al. | WO | 0072907 | 12/2000 |
| 2008/0071349 | A1 | 3/2008 | Atanasoska et al. | WO | 0135928 | 5/2001 |
| 2008/0071351 | A1 | 3/2008 | Flanagan et al. | WO | 0247581 | 6/2002 |
| 2008/0071355 | A1 | 3/2008 | Weber et al. | WO | 02060506 | 8/2002 |
| 2008/0082162 | A1 | 4/2008 | Boismier et al. | WO | 03055414 | 7/2003 |
| 2008/0086113 | A1 | 4/2008 | Tenney et al. | WO | 2004006983 | 1/2004 |
| 2008/0097349 | A1 | 4/2008 | Dillinger | WO | 2004026281 | 4/2004 |
| 2008/0097569 | A1 | 4/2008 | O'Connor et al. | WO | 2004043298 | 5/2004 |
| 2008/0147177 | A1 | 6/2008 | Scheuermann et al. | WO | 2004043292 | 7/2004 |
| 2008/0188836 | A1 | 8/2008 | Weber et al. | WO | 2004058100 | 7/2004 |
| 2008/0208325 | A1 | 8/2008 | Helmus et al. | WO | 2004064911 | 8/2004 |
| 2008/0275543 | A1 | 11/2008 | Lenz et al. | WO | 2005051450 | 6/2005 |
| 2008/0294236 | A1 | 11/2008 | Anand et al. | WO | 2005077305 | 8/2005 |
| | | | | WO | 2005082277 | 9/2005 |
| | | | | WO | 2005089673 | 9/2005 |
| | | | | WO | 2005110285 | 11/2005 |
| | | | | WO | 2006029708 A1 | 3/2006 |
| | | | | WO | 2006099450 | 9/2006 |
| | | | | WO | 2007031968 | 3/2007 |
| | | | | WO | 2007031972 | 3/2007 |
| | | | | WO | 2007059253 | 5/2007 |
| | | | | WO | 2007118139 | 10/2007 |
| | | | | WO | 2008016528 | 2/2008 |
| | | | | WO | 2008073208 | 6/2008 |

FOREIGN PATENT DOCUMENTS

| | | |
|---|---|---|
| DE | 3608158 | 9/1987 |
| DE | 19855421 | 5/2000 |
| DE | 10064596 | 6/2002 |
| DE | 10150995 | 4/2003 |
| DE | 10200387 | 8/2003 |
| DE | 102005010100 | 9/2006 |
| DE | 10107339 | 2/2009 |
| EP | 1132058 | 9/2001 |
| EP | 1159934 | 12/2001 |
| EP | 1235560 | 9/2002 |
| EP | 1236447 | 9/2002 |

\* cited by examiner

DRUG-ELUTING STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents and similar devices such as stent, stent-grafts, expandable frameworks, and similar implantable medical devices, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

To prevent thrombosis and restenosis, and to treat vasculature tissue, there is a need to provide therapeutic agents directly at the site of stent deployment. One approach is through the use of medicated stents. The embodiments of the present invention provide various stent structures for containing therapeutic agents.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided for the purposes of complying with 37 C.F.R. §1.72.

BRIEF SUMMARY OF THE INVENTION

In at least one embodiment, the invention is directed to a stent for delivering therapeutic agents to a body lumen. The stent comprises a plurality of circumferential serpentine bands with each band comprising a plurality of struts. At least one strut has at least one first well region and at least one second well region. The at least one first well region has a first thickness, and the at least one second well region has a second thickness, the first thickness being greater than the second thickness. Each well region defines a well, each well having a depth. At least some of the wells contain a therapeutic agent.

In some embodiments, at least one second well region is positioned between two first well regions.

In at least one embodiment, the depth of at least one of the wells extends completely through the thickness of the strut.

In some embodiments, the depth of at least one of the wells extends only partially through the thickness of the strut.

In at least one embodiment, the well region comprises a durable coating, the durable coating being immediately adjacent and at least partially defining at least one well.

In some embodiments, the strut further comprises a width, and at least one of the first thickness and the second thickness have a ratio to the strut width of 1:2 strut thickness:strut width, or 2:1 strut thickness:strut width, for example.

In at least one embodiment, the present invention is directed toward a method of making a stent for delivering therapeutic agents to a body lumen. The method comprises providing at least one strut having a length, a thickness, an inner side, an outer side, and a circumference. The method further comprises creating at least one well through both the coating and the strut. The method further comprises applying a durable coating along at least a portion of the length of the at least one strut. The method further comprises depositing a therapeutic agent within the at least one well.

In some embodiments, the durable coating is applied only along at least a portion of the outer side of the at least one strut.

In at least one embodiment, the durable coating is distributed substantially evenly along at least a portion of the entire outer side.

In some embodiments, the durable coating includes applying the durable coating along at least a portion of the outer side and the inner side of the at least one strut.

In at least one embodiment, the durable coating immediately adjacent the at least one well has a first thickness, the durable coating tapering to a second thickness at a distance D from the well, the second thickness being less than the first thickness.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
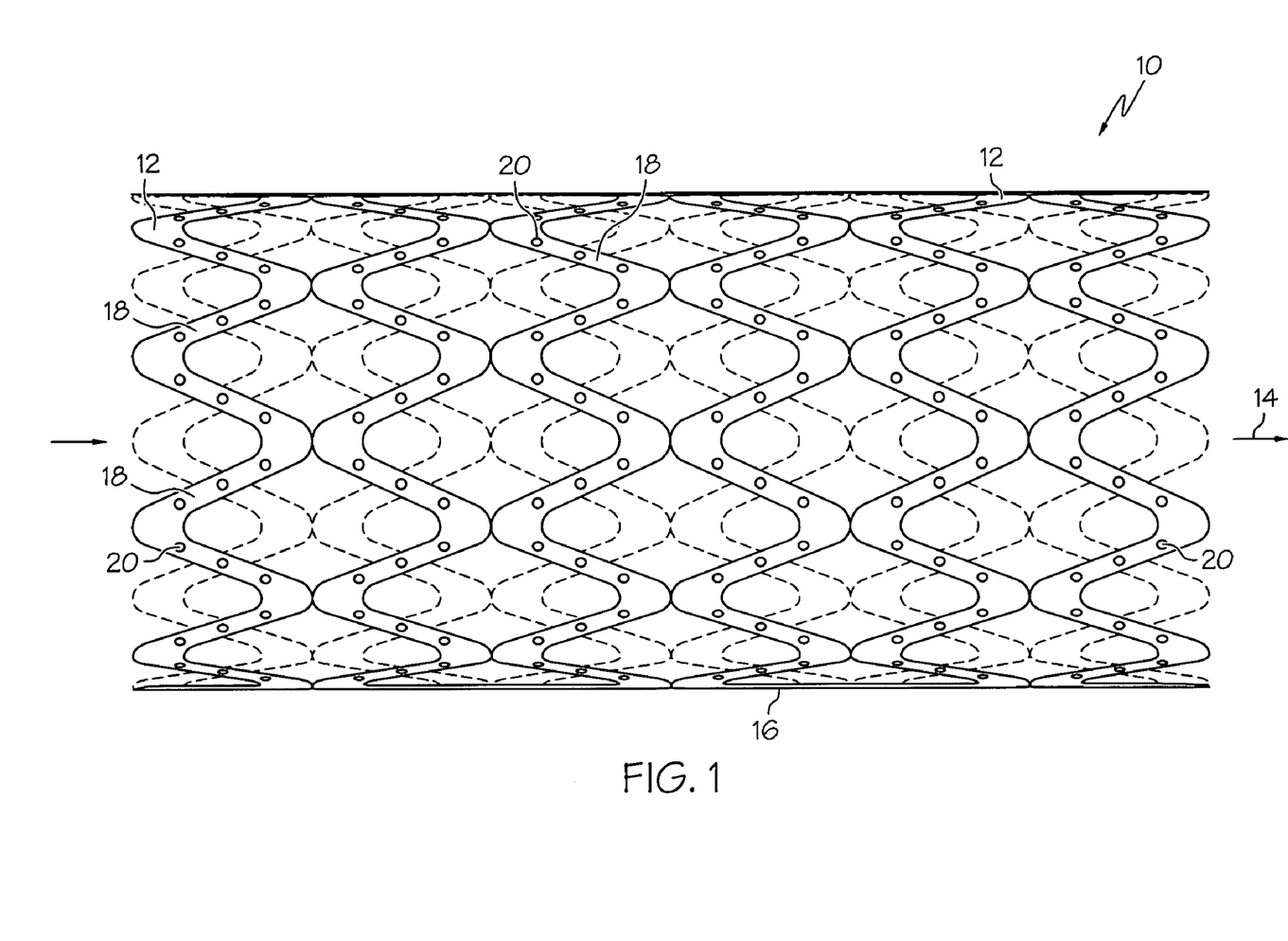
FIG. 1 is an illustration of a drug-eluting stent in accordance with one embodiment of the present invention.

FIG. 1 is an illustration of an embodiment of a stent for delivering therapeutic agents to a vessel in the body. A stent 10 comprising a plurality of serpentine bands 12 is depicted in FIG. 1. The serpentine bands are disposed about a longitudinal axis 14 and are arranged such that the stent has a generally tubular body 16. As seen in FIG. 1, the serpentine bands are comprised of a plurality of struts 18. At least some of the struts 18 include reservoirs or wells 20 (hereafter "wells"). As will be discussed in greater detail below, in some embodiments the wells 20 are loaded with therapeutic agents for delivery into a body lumen or vessel.

Figure 2:
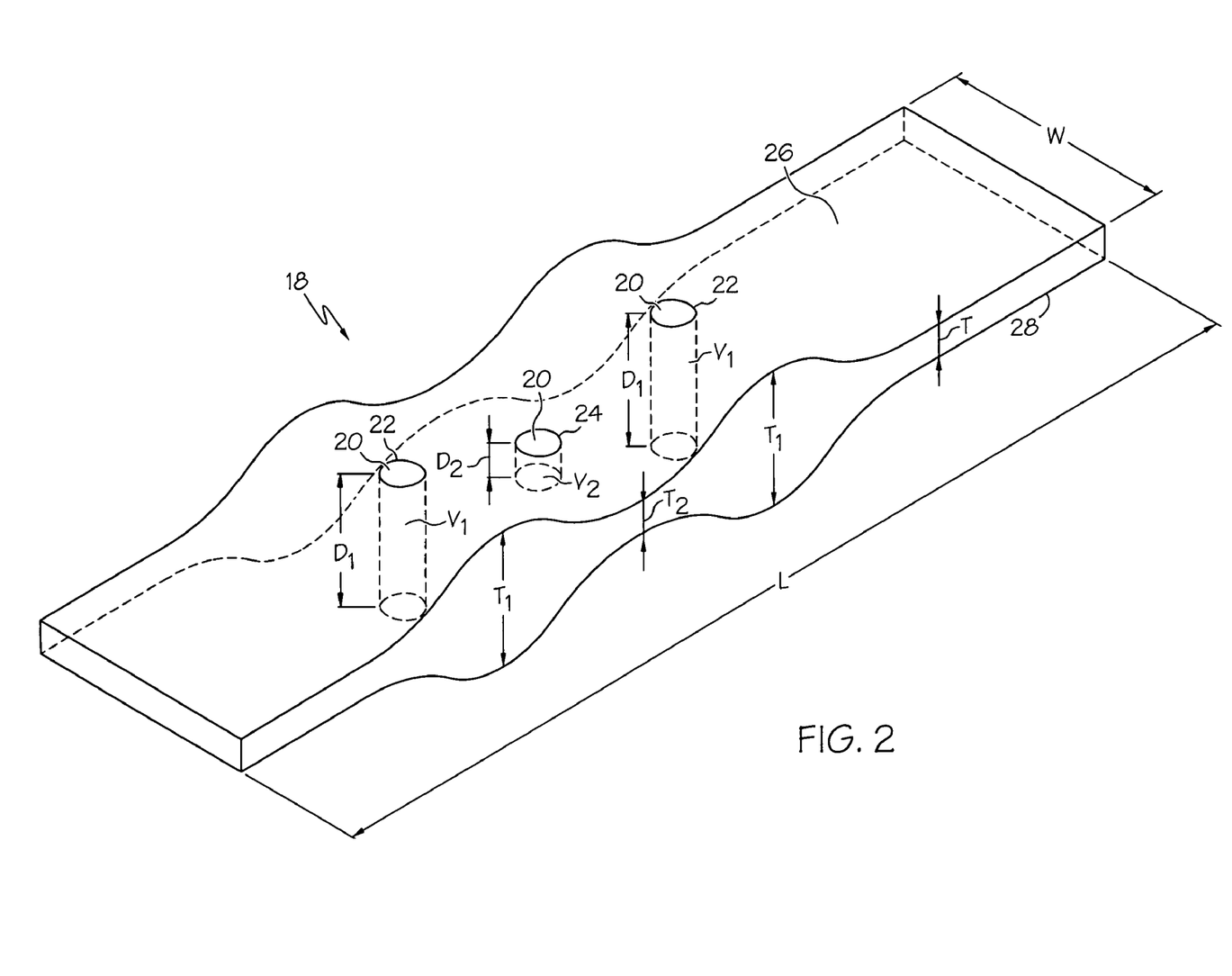
FIG. 2 is a perspective view of a strut with wells of a drug-eluting stent, in accordance with one embodiment of the present invention.

Turning now to FIG. 2, a portion of a strut 18 is depicted. Strut 18 has a variable thickness T along at least a portion of its length L. Wells 20 are placed along at least a portion of the length of the strut. In the embodiment depicted in FIG. 2, first well regions are shown at 22. A first well region 22 defines a well 20. First well regions are positioned generally at locations along the length of the strut where the thickness T is greater than adjacent regions. A second well region 24 is also depicted in FIG. 2. Second well regions are positioned generally at locations along the length of the strut where the thickness T is less than adjacent regions. For example, in FIG. 2, first well regions 22 are positioned in regions of the strut with thickness $T_1$. And, second well regions 24 are positioned in regions of the strut with thickness $T_2$, where $T_1$ is greater than $T_2$.

Figure 4:
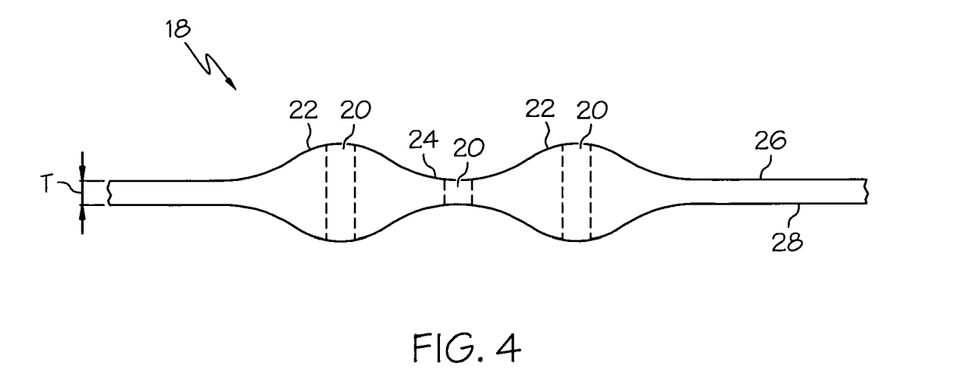
FIG. 4 is a cross-sectional view of the strut shown in FIG. 2.
Figure 5:
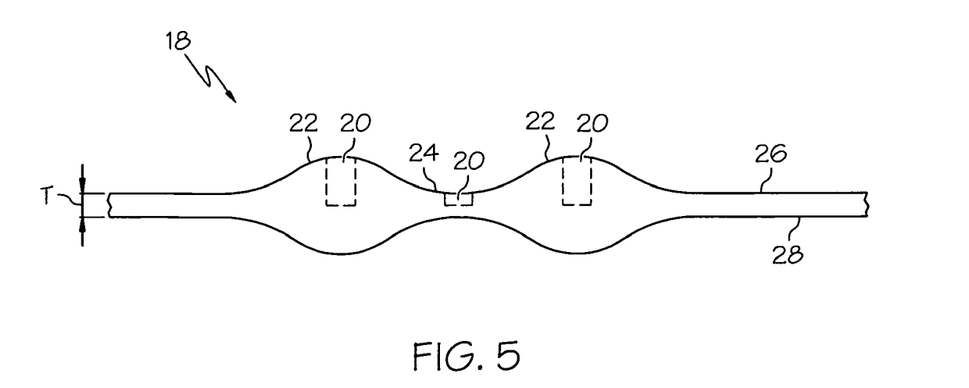
FIG. 5 is a cross-sectional view of a strut with wells in another embodiment of the present invention.

As mentioned above, the well regions 22, 24 define wells 20. Each well 20 extends at least partially through the strut material of strut 18. As such, each well 20 has a depth which may be less than or equal to the thickness of the strut. In an embodiment in which the depth of the well is equal to the thickness of the strut, such as is shown in FIG. 2 and the cross-sectional view of FIG. 4, the wells 20 extend completely through the thickness of the strut material. The well is open on both the outer surface 26 and the inner surface 28 in such an embodiment. In FIG. 2 the wells 20 of the first regions 22 have a depth $D_1$ and volume $V_1$, while the well 20 of the second region 24 has a depth $D_2$ and volume $V_2$, $D_1$ being greater than $D_2$. In an embodiment in which the depth of the well is less than the thickness of the strut, such as is shown in the cross-sectional view of FIG. 5, the wells 20 extend only partially through the thickness of the strut material such that the well is open on one of either the outer surface 26 or the inner surface 28.

It should be clear that if the wells have substantially the same dimensions with the exception of depth, than the volume $V_1$ of the deeper wells of the first regions 22 is greater than the volume $V_2$ of the wells located in the second regions 24. Thus the deeper wells, when filled substantially full with a therapeutic agent, provide an increased volume of therapeutic agent for delivery in comparison to wells that are less deep. Furthermore, deeper wells allow use of a barrier layer to provide a directional release gradient for the therapeutic agent, while less deep wells without such a barrier elute bidirectionally. Finally, deep wells provide a sustained release of therapeutic agent while less deep wells provide bolus doses.

In some embodiments of the invention, the strut includes two first well regions 22 separated by a second well region 24, as in FIG. 2. In at lease some embodiments, a thick-thin-thick strut design is necessary to improve the mechanical performance of the strut. Embodiments of the present invention take advantage of this necessity by placing wells within the thick-thin-thick portions in order to optimize the release of therapeutic agent into the body.

In at least one embodiment, provided along the length of the strut is a repeating pattern of a first well region, followed then by a second well region, followed then by a first well region, and followed then by a second well region, repeating as desired. In some embodiments, a strut is provided that has a single first well region followed by one or more second well regions. There are numerous first well region and second well region combinations that one of ordinary skill in the art would recognize. All of these combinations, while not explicitly detailed herein, are considered to form a portion of this disclosure.

Figure 3:
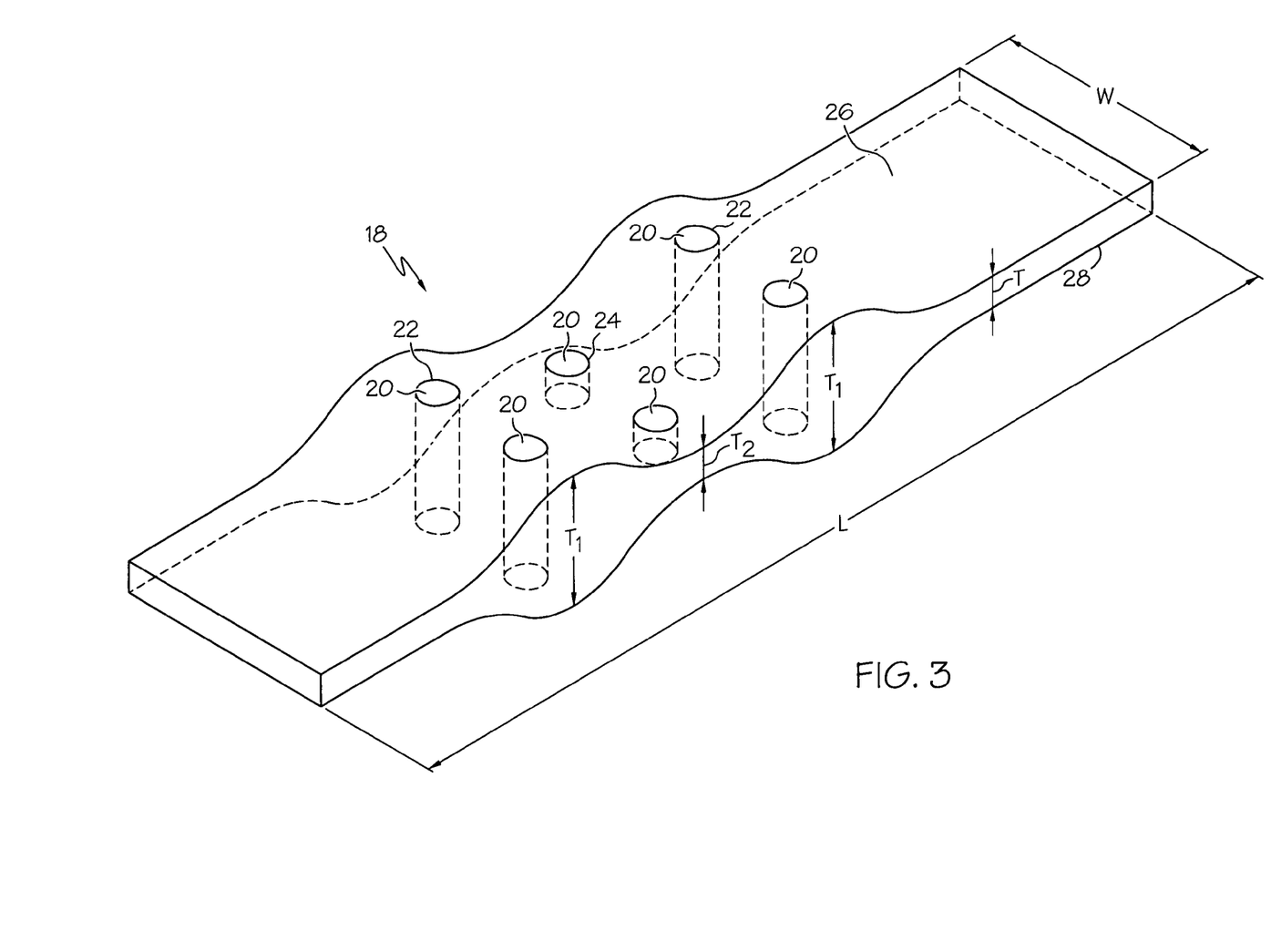
FIG. 3 is a perspective view of a strut with wells of a drug-eluting stent, in accordance with one embodiment of the present invention.

In some embodiments, a plurality of holes within a well region is included to increase the amount of therapeutic agent which can be delivered to the site of implantation, as shown in FIG. 3. The first regions 22 and the second region 24 of FIG. 3 depict multiple holes within each well region 22, 24 in the strut 18.

Referring again to FIG. 2, it should be noted that the additional strut material which forms the added thickness of a first well region 22 extends both outwardly from the outer surface 26 of the strut as well as inwardly from the inner surface of the strut 28. This is in contrast to the embodiment depicted in FIG. 6.

Figure 6:
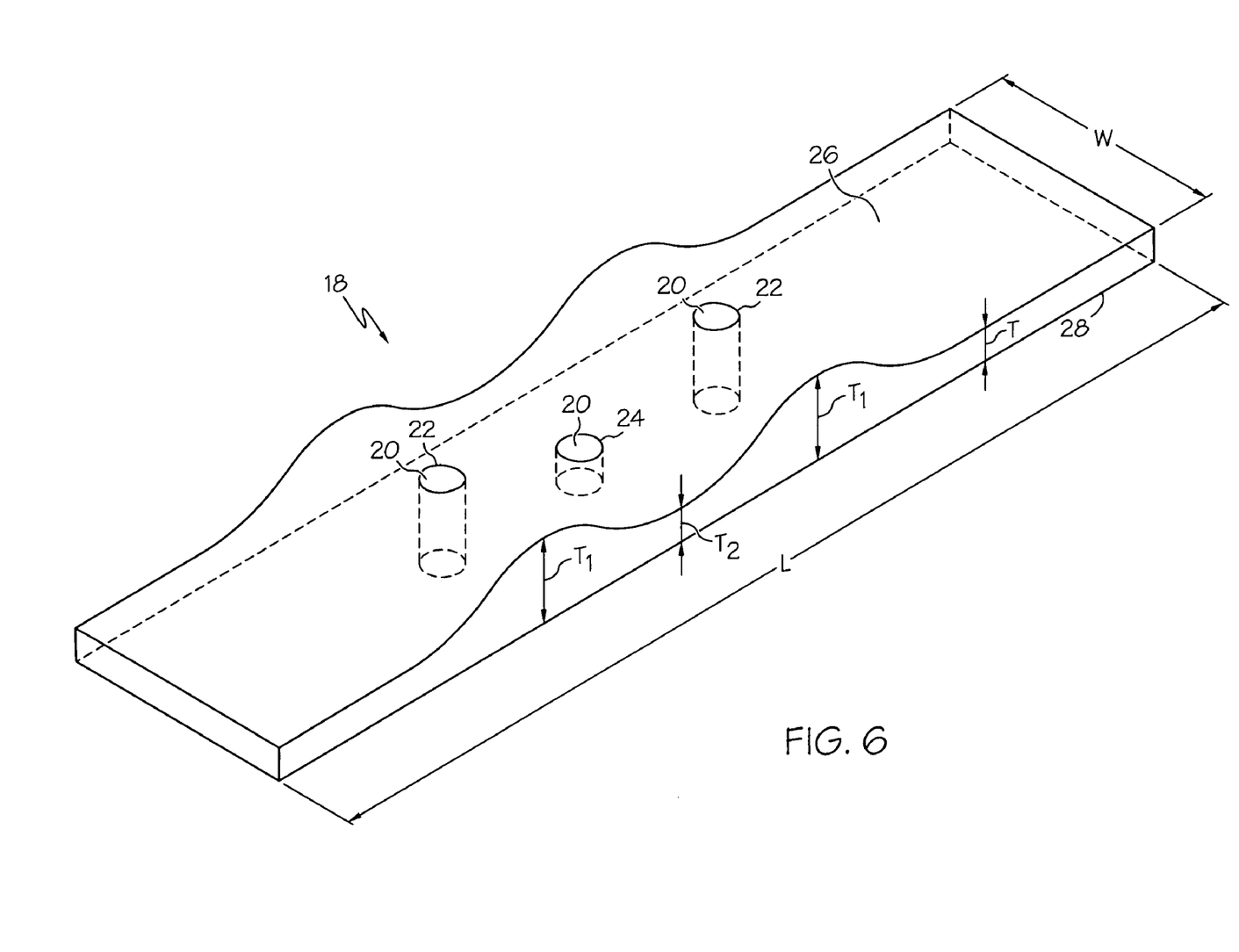
FIG. 6 is a perspective view of a strut with wells of a drug-eluting stent, in accordance with one embodiment of the present invention.

As illustrated in FIG. 6, the strut material which forms the added thickness of a first well region 22 extends only outwardly from the outer surface 26 of the strut. In an alternate embodiment, the extra strut material extends only inwardly from the inner surface 28 of the strut.

Figure 7:
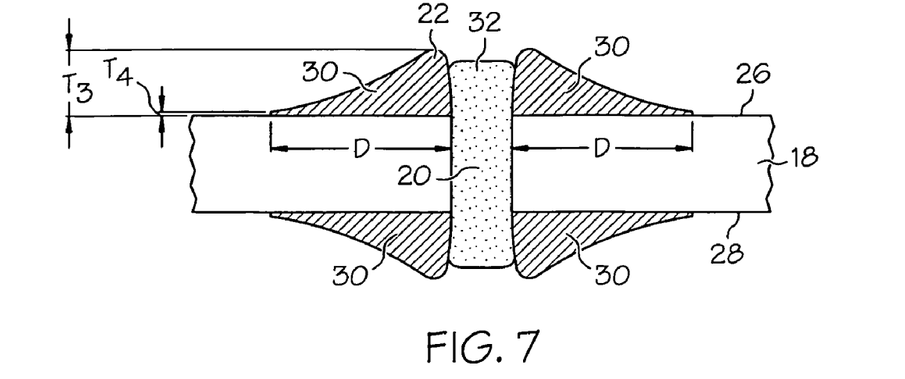
FIG. 7 is a cross-sectional view of a strut with a durable coating, in accordance with one embodiment of the present invention.
Figure 8:
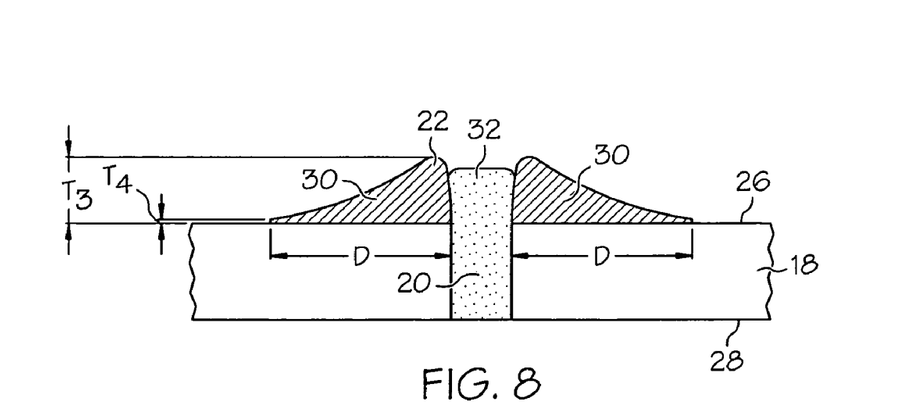
FIG. 8 is a cross-sectional view of a strut with a durable coating, in accordance with one embodiment of the present invention.
Figure 9:
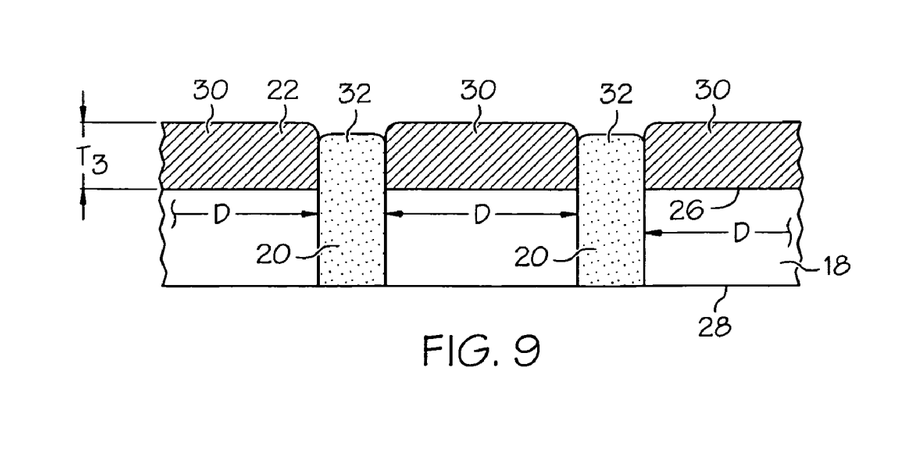
FIG. 9 is a cross-sectional view of a strut with a durable coating, in accordance with one embodiment of the present invention.

Referring now to FIGS. 7-9, in some embodiments the well region 22 may comprise a durable coating 30. The durable coating 30 is placed immediately adjacent a well 20 such that it partially defines the well. Or, the durable coating 30 may be placed, as desired, onto a strut such that a well may then be created through the durable coating. In at least one embodiment, the well is created through at least a portion of the strut material. The well may be created through the durable coating and strut material by any technique known by those of ordinary skill in the art, including, but not limited to, chemical etching and laser ablation.

FIG. 7 depicts a strut 18 with a durable metallic or ceramic coating 30 placed on both the outer surface 26 and the inner surface of the strut. Durable coatings may be employed near the wells 20 to increase the overall volume of therapeutic agent 30 that can be contained within the well. In at least one embodiment, it may be desirable to apply the durable coating about the entire circumference of at least a portion of the length of a strut such that at least a portion of the outer surface, the inner surface, and the sides of the strut have the durable coating applied to them. The term circumference is meant to include the boundary of a strut, regardless of the cross-sectional characteristics of the strut. Thus, a strut with a square, rectangular, circular, semi-circular, or elliptical cross-section, or any other cross-sectional shape, has a circumference as the term is used herein.

FIG. 8 depicts a strut 18 with a durable coating 30 on only one surface of the strut, shown here as the outer surface 26. One of ordinary skill will recognize that it the durable coating can be deposited on the inner surface of the strut rather than the outer surface.

FIGS. 7-8 both depict struts with durable coatings 30 applied such that the thickness of the durable coating 30 tapers from a thickness $T_3$ immediately adjacent the well 20 to a smaller thickness $T_4$ as the distance D from the well 20 increases. In contrast, FIG. 9 depicts a strut with a durable coating having a thickness $T_3$ such that as the distance D from the well increases, the thickness of the $T_3$ remains substantially constant. Although in FIG. 9 the coating 30 is applied only on the outer surface 26, one of ordinary skill will recognize that the coating can be placed on both the outer and inner surfaces, or on only the inner surface.

One of ordinary skill in the art will recognize that there are a number of materials available that may be used as a durable coating. A non-limiting list of suitable materials includes the following: iridium oxide (IrOx), titanium oxide (TiOx), titanium dioxide ($TiO_2$), chromium oxide (CrOx), titanium-nitrious-oxide (TiNOx), and diamond-like carbon (DLC).

Referring again to FIGS. 7-9, wells 20 are shown to contain therapeutic agent 32. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate. In at least one embodiment, the polymer agent can be biodegradable (e.g. PLA, PLGA, etc.).

In some embodiments at least a portion of the stent is configured to include one or more additional mechanisms for the delivery of a therapeutic agent. Often the agent will be in the form of a coating or other layer (or layers) of material placed on a surface region of the stent, which is adapted to be released at the site of the stent's implantation or areas adjacent thereto.

In at least one embodiment of the present invention, the recoil of the stent may be reduced by optimizing the aspect ratio of the stent. That is, by increasing the thickness of the struts, and by decreasing the width of the struts, the recoil may be reduced. Desirable ratios of thickness to width are in the range of 1:2 strut thickness:strut width, or 2:1 strut thickness:strut width, for example. In such an embodiment, it may be desirable to reduce the diameter of the well to accommodate the narrower strut. In addition to reducing the recoil, the narrower strut provides the stent with a smaller profile while it is in a crimped state. The crimped profile refers to the amount of metal present in a circumferential section while the stent is crimped. The crimped profile of the stent is directly related to the ability to cross small lumen lesions.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. At least one embodiment of the present invention is directed toward a bifurcated stent having struts with wells.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent for delivering therapeutic agents to a body lumen, the stent comprising:

a plurality of circumferential serpentine bands, each band comprising a plurality of struts, each strut having an outer surface, an inner surface, and a strut thickness between the outer surface and the inner surface, the strut thickness being variable along at least a portion of a length of the strut, at least one strut located on the strut at at least one first well region and at least one second well region, the at least one first well region located on the strut at a first strut thickness, the at least one second well region having a second strut thickness, the first strut thickness being greater than the second strut thickness, each well region defining at least one well, each well having a depth extending from the outer surface of the strut through at least a portion of the strut thickness, at least some of the wells containing a therapeutic agent.

2. The stent of claim 1, wherein each well has a volume, the at least one well defined by the at least one first well region having a first volume, the at least one well defined by the at least one second well region having a second volume, the first volume being greater than the second volume.

3. The stent of claim 1, wherein at least one second well region is positioned between two first well regions.

4. The stent of claim 1, wherein the depth of at least one of the wells extends completely through the strut thickness.

5. The stent of claim 1, wherein the well region comprises a durable coating, the durable coating being immediately adjacent and at least partially defining at least one well.

6. The stent of claim 1, wherein the strut further comprises a width, and wherein at least one of the first thickness and the second thickness have a ratio to the strut width of 1:2.

7. The stent of claim 1, wherein the strut further comprises a width, and wherein at least one of the first thickness and the second thickness have a ratio to the strut width of 2:1.

* * * * *